(12) United States Patent
Jang et al.

(10) Patent No.: US 8,742,157 B2
(45) Date of Patent: Jun. 3, 2014

(54) METHOD OF PREPARING BIPHENYL-4-YL DIPHENYL PHOSPHATE COMPOSITION

(75) Inventors: Won Seok Jang, Daejeon (KR); Won Yeob Kim, Daejeon (KR); Myoung Lae Kim, Daejeon (KR)

(73) Assignee: SK Innovation Co., Ltd. (KR)

( * ) Notice: Subject to any disclaimer, the term of this patent is extended or adjusted under 35 U.S.C. 154(b) by 0 days.

(21) Appl. No.: 13/809,986

(22) PCT Filed: Jul. 13, 2011

(86) PCT No.: PCT/KR2011/005138
§ 371 (c)(1),
(2), (4) Date: Feb. 12, 2013

(87) PCT Pub. No.: WO2012/008744
PCT Pub. Date: Jan. 19, 2012

(65) Prior Publication Data
US 2013/0178642 A1    Jul. 11, 2013

(30) Foreign Application Priority Data
Jul. 14, 2010  (KR) ........................ 10-2010-0067689

(51) Int. Cl.
*C07F 9/06* (2006.01)
(52) U.S. Cl.
USPC .............................................. 558/90; 558/87

(58) Field of Classification Search
USPC ................................................ 558/87, 92, 90
See application file for complete search history.

(56) References Cited

U.S. PATENT DOCUMENTS

| | | | |
|---|---|---|---|
| 2,225,285 A | 12/1940 | Moyle | |
| 2,656,373 A | 10/1953 | Gamrath | |
| 6,204,404 B1 * | 3/2001 | Tokuyasu et al. | ............... 558/92 |
| 6,242,154 B1 * | 6/2001 | Grasshoff et al. | .......... 430/270.1 |
| 7,557,152 B2 * | 7/2009 | Kanno et al. | .................. 524/126 |
| 2010/0168299 A1 | 7/2010 | Tanaka et al. | |

FOREIGN PATENT DOCUMENTS

| | | |
|---|---|---|
| EP | 0595597 | 10/1993 |
| KR | 1020070112167 | 11/2007 |

OTHER PUBLICATIONS

International Search Report—PCT/KR2011/005138 dated Feb. 21, 2012.
European Search Report—European Application No. 11807029.1 issued on Dec. 16, 2013 citing EP 0 595 597.

* cited by examiner

*Primary Examiner* — Golam M M Shameem
(74) *Attorney, Agent, or Firm* — Cantor Colburn LLP

(57) ABSTRACT

Provided is a method of preparing a biphenyl-4-yl diphenyl phosphate composition for use as a flame retardant or a plasticizer for resin, including mixing phosphoryl chloride ($POCl_3$), 4-phenylphenol, and a catalyst, so that first dehydrochlorination occurs; and further adding phenol, so that second dehydrochlorination occurs.

7 Claims, No Drawings

METHOD OF PREPARING BIPHENYL-4-YL DIPHENYL PHOSPHATE COMPOSITION

TECHNICAL FIELD

The present invention relates to a method of preparing a biphenyl-4-yl diphenyl phosphate (hereinafter referred to as "BDP") composition suitable for use as a photo-sensitive material, a plasticizer, or a flame retardant for general-purpose resin.

BACKGROUND ART

Currently, a phosphorus-based flame retardant is mainly available in lieu of a halogen-based flame retardant, and examples thereof include red phosphorus, phosphoric acid ester or phosphate, phosphonate, phosphinate, phosphine oxide, phosphazene, etc.

Red phosphorus which is a compound composed exclusively of phosphorus is used to a limited extent because of the probability of generating phosphine ($PH_3$) during processing or is being used via surface coating, which makes it difficult to show different colors and thus has limited end-uses.

Particularly useful as the flame retardant is a phosphate. According to a flame-retarding mechanism, a phosphorus-based flame retardant, which is regarded as important in terms of flame-retarding effects in solid phase, unlike a halogen-based flame retardant, has difficulty in imparting flame retardancy to styrene, acryl, and olefin polymers themselves which do not form char upon combustion, and is thus used by being blended with a polymer that facilitates the formation of char, for example, PC, PPE, phenol resin, etc.

A phosphoric acid ester-based flame retardant may be used as a plasticizer for resin, and has been initially utilized as a flame retardant and a plasticizer for polyurethane. For example, triphenylphosphate (TPP), which has begun to be widely used as a flame retardant for PC/ABS and PPO/HIPS for PPE- and PC-based blends, is further receiving attention after halogen-related problems are on the rise. However, because TPP is very highly volatile, it may volatilize during processing of flame-retarding resin, undesirably causing appearance defects due to gas clustering or carbonization. Furthermore, the volatilized gas accumulates in corners of the injection molded product, and thus may develop into cracks over time. As an alternative to TPP, resorcinol bis(diphenylphosphate) (RDP) which has improved volatility and an increased molecular weight has been employed, but is comparatively poor in terms of hydrolysis resistance. Hence, bisphenol bis(diphenylphosphate) having bisphenol in place of resorcinol as a connection chain is currently widely available because it has good hydrolysis resistance and is price competitive. However, bisphenol bis(diphenylphosphate) is problematic because it is difficult to process and is insufficiently plasticized.

DISCLOSURE OF INVENTION

Technical Problem

Therefore, an object of the present invention is to provide a biphenyl-4-yl diphenyl phosphate (BDP) composition, suitable for use as a silver halide photosensitive material, a plasticizer of a cellulose triacetate film adapted for a liquid crystal image display, or a flame retardant for a halogen free type resin. The BDP composition may include triphenylphosphate (TPP), BDP, bis(para-biphenyl)phenyl phosphate (DBP), and tribiphenylphosphate (TBP). In cases where the composition according to the present invention is used as a plasticizer, when the amount of TPP is high, mechanical properties of resin may deteriorate, and when the amount of DBP is high, plasticization effects may become insufficient, and thus the amount of BDP is increased, thereby ensuring superior plasticization effects while preventing the mechanical properties of resin from deteriorating.

Solution to Problem

In one general aspect, the present invention provides a method of preparing a BDP composition represented by Formula 1 below suitable for use as a flame retardant or a plasticizer for resin, the method comprising mixing phosphoryl chloride ($POCl_3$), 4-phenylphenol, and a catalyst, so that first dehydrochlorination occurs; and further adding phenol, so that second dehydrochlorination occurs, thus satisfying $0.60 \leq C_{n=2} \leq 0.95$ ($C_{n=2}$ is a composition in which n is 2 in Formula 1).

[Formula 1]

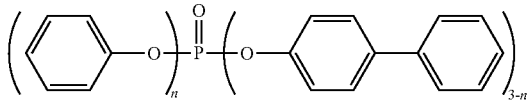

(wherein n is an integer of 0~3).

Hereinafter, a detailed description will be given of the present invention.

The preparation of the BDP composition represented by Formula 1 according to the present invention may include mixing phosphoryl chloride ($POCl_3$), 4-phenylphenol, and a catalyst, so that first dehydrochlorination occurs, and further adding phenol, so that second dehydrochlorination occurs.

As such, phosphoryl chloride upon first dehydrochlorination may be contained at a molar ratio of 1:2.7~1:3.0 to a sum of 4-phenylphenol upon first dehydrochlorination and phenol upon second dehydrochlorination. If the molar ratio is less than the lower limit of the above range, the yield of BDP may decrease. In contrast, if the molar ratio exceeds the upper limit of the above range, unreacted phenols may remain behind.

In the present invention, the molar ratio of 4-phenylphenol upon first dehydrochlorination to phenol upon second dehydrochlorination may be adjusted in the range of 1:1.8~1:3.0. If the molar ratio is less than the lower limit of the above range, chlorine gas may undesirably volatilize. In contrast, if the molar ratio exceeds the upper limit of the above range, unreacted 4-phenylphenol may remain behind.

Upon first dehydrochlorination, the catalyst may comprise any one selected from the group consisting of anhydrous aluminum chloride, anhydrous aluminum fluoride, anhydrous magnesium chloride, anhydrous magnesium fluoride, anhydrous manganese chloride, anhydrous manganese fluoride, anhydrous ferrous chloride, anhydrous ferric chloride, anhydrous ferrous fluoride, anhydrous ferric fluoride, and mixtures thereof.

Also, the first dehydrochlorination may be performed at −20~0° C. If the reaction temperature is higher than 0° C., phosphoryl chloride and hydrochloric acid gas generated by this dehydrochlorination may volatilize, or unreacted phenols may be left behind, and the selectivity for the resulting BDP composition may decrease.

Also, the second dehydrochlorination may be performed at 20~50° C., and preferably 25~50° C. If the reaction temperature falls outside of the above range, the reaction rate may decrease or the unreacted remainder may occur.

As mentioned above, the BDP composition according to the present invention in which the amounts of triphenylphosphate (TPP) and tribiphenylphosphate (TBP) are adjusted can play a role as a flame retardant or a plasticizer for resin and can exhibit enhanced mechanical strength and superior thermal properties.

Advantageous Effects of Invention

According to the present invention, a BDP composition can reduce the production cost, and can produce triphenylphosphate (TPP) and tribiphenylphosphate (TBP) in respective amounts of less than 1 wt %, thus enhancing mechanical strength and exhibiting very high thermal properties. Furthermore, the BDP composition according to the present invention is useful as a flame retardant for general-purpose resin, a silver halide photosensitive material, or a plasticizer of a cellulose triacetate film for use in a liquid crystal image display.

BEST MODE FOR CARRYING OUT THE INVENTION

A better understanding of the present invention may be obtained via the following examples that are set forth to illustrate, but are not to be construed as limiting, the present invention.

Example 1

Into a 3 L glass reactor equipped with a stirrer, a dichloromethane solvent was introduced, and a thermometer was provided to measure the inner temperature of the reactor. The inside of the reactor was replaced with nitrogen gas, and stirring was initiated while decreasing the temperature of the reactor to 0° C. After the reaction temperature was lowered up to 0° C., 869 g (5.67 mol) of phosphoryl chloride, 963 g (5.67 mol) of 4-phenylphenol, anhydrous manganese chloride, and a base were added in droplets thereto.

The stirring was performed for 2 hours. When 4-phenylphenol was completely used for reaction, 1067 g (11.33 mol) of phenol was further added in droplets thereto. Thereafter, the temperature of the reactor was increased to 25° C. After completion of the reaction, the reaction product was washed several times with water and dried with magnesium chloride. The dried reaction product was distilled under reduced pressure to thus remove an excess of solvent, thereby obtaining a desired BDP composition. The BDP composition thus obtained was quantitatively analyzed using liquid chromatography. The results are shown in Table 1 below.

Example 2

A BDP composition was prepared in the same manner as in Example 1, with the exception that the molar ratio of phosphoryl chloride and 4-phenylphenol was 1:0.7, after which the BDP composition was quantitatively analyzed using liquid chromatography. The results are shown in Table 1 below.

Example 3

A BDP composition was prepared in the same manner as in Example 1, with the exception that the stirring was performed not at 0° C. but at −20° C., after which the BDP composition was quantitatively analyzed using liquid chromatography. The results are shown in Table 1 below.

Example 4

A BDP composition was prepared in the same manner as in Example 3, with the exception that the molar ratio of phosphoryl chloride and 4-phenylphenol was 1:1.1 and 1014 g (10.77 mol) of phenol was added in droplets thereto, after which the BDP composition was quantitatively analyzed using liquid chromatography. The results are shown in Table 1 below.

Example 5

A BDP composition was prepared in the same manner as in Example 1, with the exception that the stirring was performed not at 25° C. but at 50° C., after which the BDP composition was quantitatively analyzed using liquid chromatography. The results are shown in Table 1 below.

Comparative Example 1

A BDP composition was prepared in the same manner as in Example 1, with the exception that the anhydrous manganese chloride catalyst was not added, after which the BDP composition was quantitatively analyzed using liquid chromatography. The results are shown in Table 1 below.

Comparative Example 2

A BDP composition was prepared in the same manner as in Example 1, with the exception that the molar ratio of phosphoryl chloride and 4-phenylphenol was 1:1.5 and 683 g (8.51 mol) of phenol was added thereto, after which the BDP composition was quantitatively analyzed using liquid chromatography. The results are shown in Table 1 below.

Comparative Example 3

A BDP composition was prepared in the same manner as in Example 1, with the exception that the stirring was performed not at 0° C. but at 25° C., after which the BDP composition was quantitatively analyzed using liquid chromatography. The results are shown in Table 1 below.

Results of Analysis by Liquid Chromatography

The amounts of the BDP compositions of Examples 1 to 5 and Comparative Examples 1 to 3 were measured using Agilent 1200 HPLC. The results are shown in Table 1 below. As such, the measurement was performed under conditions of acetonitrile/water=85/15, a feed amount of 10 µl, an oven temperature of 40° C., a total flow rate of 1.0 ml/min, and a measurement time of 20 minutes.

TABLE 1

Results of Analysis by Liquid Chromatography

|  | TPP (wt %) | BDP (wt %) | DBP (wt %) | TBP (wt %) | Unconfirmed Material (wt %) |
|---|---|---|---|---|---|
| Ex. 1 | 5.2 | 79.0 | 14.8 | 0.0 | 1.0 |
| Ex. 2 | 20.9 | 67.0 | 10.0 | 0.0 | 2.1 |
| Ex. 3 | 0.5 | 85.4 | 13.6 | 0.0 | 0.5 |
| Ex. 4 | 0.3 | 93.2 | 6.0 | 0.0 | 0.5 |
| Ex. 5 | 5.0 | 80.2 | 13.8 | 0.0 | 1.0 |
| C. Ex. 1 | 13.0 | 65.4 | 20.2 | 0.1 | 1.3 |
| C. Ex. 2 | 0.7 | 62.5 | 31.5 | 3.8 | 1.5 |
| C. Ex. 3 | 34.8 | 43.0 | 15.4 | 5.0 | 1.8 |

As is apparent from the above table, the examples according to the present invention can be seen to be a BDP composition containing 60~95 wt % of biphenyl-4-yl diphenyl phosphate, and thus improved mechanical properties and plasticization effects can be expected.

The invention claimed is:

1. A method of preparing a biphenyl-4-yl diphenyl phosphate composition represented by Formula 1 below, comprising:

mixing phosphoryl chloride (POCl$_3$), 4-phenylphenol, and an anhydrous metal halide catalyst, so that first dehydrochlorination occurs; and further adding phenol, so that second dehydrochlorination occurs, thus satisfying $0.60 \leq C_{n=2} \leq 0.95$, wherein $C_{n=2}$ is a composition in which n is 2 in Formula 1:

Formula 1

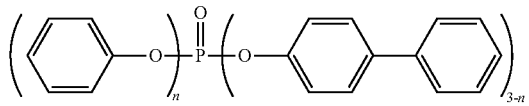

wherein n is an integer of 0 to 3.

2. The method of claim 1, wherein the phosphoryl chloride is contained at a molar ratio of 1:2.7~1:3.0 to a sum of 4-phenylphenol upon first dehydrochlorination and phenol upon second dehydrochlorination.

3. The method of claim 1, wherein a molar ratio of the 4-phenylphenol upon first dehydrochlorination to the phenol upon second dehydrochlorination is 1:1.8~1:3.0.

4. The method of claim 1, wherein the catalyst comprises any one selected from the group consisting of anhydrous aluminum chloride, anhydrous aluminum fluoride, anhydrous magnesium chloride, anhydrous magnesium fluoride, anhydrous manganese chloride, anhydrous manganese fluoride, anhydrous ferrous chloride, anhydrous ferric chloride, anhydrous ferrous fluoride, anhydrous ferric fluoride, and mixtures thereof.

5. The method of claim 1, wherein the first dehydrochlorination is performed at a temperature of −20~0° C.

6. The method of claim 1, wherein the second dehydrochlorination is performed at a temperature of 20~50° C.

7. The method of claim 2, wherein a molar ratio of the 4-phenylphenol upon first dehydrochlorination to the phenol upon second dehydrochlorination is 1:1.8~1:3.0.

* * * * *